United States Patent
Chang et al.

(10) Patent No.: US 11,292,827 B2
(45) Date of Patent: Apr. 5, 2022

(54) METHOD FOR PRODUCING HIGH-CONCENTRATION COLLAGEN FOR USING AS MEDICAL MATERIAL

(71) Applicant: SEWONCELLONTECH CO., LTD., Seoul (KR)

(72) Inventors: Cheong Ho Chang, Seoul (KR); Hyeong Woo Jeong, Goyang-si (KR); Ji Chui Yoo, Namyangju-si (KR); Se Ken Yeo, Suwon-si (KR); Dong Sam Suh, Seoul (KR)

(73) Assignee: SEWONCELLONTECH CO., LTD., Seoul (KR)

( * ) Notice: Subject to any disclaimer, the term of this patent is extended or adjusted under 35 U.S.C. 154(b) by 808 days.

(21) Appl. No.: 15/527,500

(22) PCT Filed: Dec. 11, 2014

(86) PCT No.: PCT/KR2014/012176
§ 371 (c)(1),
(2) Date: May 17, 2017

(87) PCT Pub. No.: WO2016/080578
PCT Pub. Date: May 26, 2016

(65) Prior Publication Data
US 2017/0334969 A1    Nov. 23, 2017

(30) Foreign Application Priority Data

Nov. 21, 2014  (KR) .......................... 10-2014-0163800

(51) Int. Cl.
| | |
|---|---|
| C07K 1/02 | (2006.01) |
| C07K 1/14 | (2006.01) |
| C07K 14/78 | (2006.01) |
| A61L 27/24 | (2006.01) |
| A61L 27/36 | (2006.01) |
| C07K 1/34 | (2006.01) |
| A61K 38/00 | (2006.01) |

(52) U.S. Cl.
CPC .............. *C07K 14/78* (2013.01); *A61L 27/24* (2013.01); *A61L 27/3683* (2013.01); *A61L 27/3687* (2013.01); *C07K 1/145* (2013.01); *C07K 1/34* (2013.01)

(58) Field of Classification Search
CPC ....................................................... C17K 1/14
See application file for complete search history.

(56) References Cited

U.S. PATENT DOCUMENTS

| | | | |
|---|---|---|---|
| 4,894,441 A | 1/1990 | Menicagli | |
| 6,569,437 B1 * | 5/2003 | Bishop ..................... | A61K 8/23 424/400 |
| 2003/0205839 A1 * | 11/2003 | Bachrach .................. | D01F 4/00 264/183 |
| 2007/0219128 A1 | 9/2007 | Chen et al. | |
| 2008/0118947 A1 * | 5/2008 | Yu .......................... | C07K 14/78 435/68.1 |
| 2008/0269119 A1 * | 10/2008 | Griffith ................. | A61F 9/0017 514/6.9 |
| 2011/0189301 A1 * | 8/2011 | Yang ....................... | A61K 35/48 424/582 |
| 2011/0257087 A1 * | 10/2011 | Krul ..................... | A23C 9/1526 514/4.9 |

FOREIGN PATENT DOCUMENTS

| | | |
|---|---|---|
| JP | 2001-200000 A | 7/2001 |
| JP | 2011-201837 A | 10/2011 |
| KR | 10-2010-0111383 A | 10/2010 |
| KR | 10-2011-0058757 A | 6/2011 |
| KR | 10-1105603 B1 | 1/2012 |
| KR | 10-2011-0068948 A | 2/2013 |
| KR | 2014-0091435 A | 7/2014 |
| KR | 10-2014-0122532 A | 10/2014 |

OTHER PUBLICATIONS

Bae et al. (2012) Virus Inactivation during the Manufacture of a Collagen Type I from Bovine Hides; Korean J. Microbiol., vol. 48, pp. 314-318.*

* cited by examiner

Primary Examiner — Manjunath N Rao
Assistant Examiner — Samuel W Liu
(74) Attorney, Agent, or Firm — Novick, Kim & Lee, PLLC; Jae Youn Kim

(57) ABSTRACT

Disclosed is a method of producing high-concentration collagen for use as a medical material, including: washing tissue of a mammal; subjecting the washed tissue to crushing and immersion in ethyl alcohol; subjecting the tissue to enzymatic treatment with stirring in purified water containing phosphoric acid and pepsin; adding sodium chloride to the collagen subjected to enzymatic treatment, performing stirring, and aggregating collagen; dissolving the aggregated collagen in purified water to give a collagen solution, which is then filtered using a filter and concentrated by removing the pepsin, low-molecular-weight material, and sodium chloride from the collagen solution using a tangential flow filtration device; subjecting the concentrated collagen to sterile filtration, aggregating the collagen using a pH solution in a neutralization tank, and concentrating the collagen by removing a non-aggregated solution; and concentrating the concentrated collagen using a centrifuge and stirring the concentrated collagen using a mixer.

3 Claims, 2 Drawing Sheets

METHOD FOR PRODUCING HIGH-CONCENTRATION COLLAGEN FOR USING AS MEDICAL MATERIAL

TECHNICAL FIELD

The present invention relates to a method of producing high-concentration collagen suitable for use as a medical material, and more particularly to a method of producing high-concentration collagen, in which collagen may be prepared at various concentrations so as to be suitable for use as a medical material, and especially high-concentration collagen may exhibit superior performance for a corresponding purpose and may be easily stored compared to low-concentration collagen. Furthermore, the present invention enables improvements in the quality and reliability of products to thereby satisfy diverse needs of consumers, who are the users thereof, and is thus very useful.

BACKGROUND ART

Collagen is a protein that is distributed in various tissues of animals and constitutes about 30% of total protein weight thereof.

Typically, collagen is a fibrous protein, and is one of the proteins that make up the skin, bones and tendons. It is mainly distributed in connective tissues of the body, and human bodies contain about 20% protein, collagen constituting about 30% thereof. Collagen has a triple-helix molecular structure configured such that three polypeptide chains are wound around each other and linked via hydrogen bonds. Collagen having such a structure plays a role in exhibiting adhesion of cells, support of body and organs, activation of cell functions, cell proliferation, hemostasis, and immunity, and moreover, collagen is responsible for organic functions of the body while forming the same, and is thus a protein that is essential for the body.

Collagen, thanks to the above properties, is currently utilized as a material or additive in various fields including those of beauty, health drinks, health foods, medicines and cosmetics, and applications thereof are gradually expanding by virtue of the functional properties thereof.

As described above, in order to separate collagen from tissue after collecting bones and leather from cattle and pigs, collagen may be obtained as an insoluble material through extraction with an organic solvent, acid/base treatment, and then addition of trypsin and hyaluronidase, but the molecular weight thereof is high and thus it is difficult to digest and absorb in the human body, and collagen is decreased in purity due to various impurities contained therein, and the field of use thereof is limited, which is undesirable.

About 20 types of collagen are currently known, among which Type 1 collagen is the most abundant, is morphologically present as a fibrous solid, and is configured such that three-stranded polypeptides are twisted through hydrogen bonding, with a molecular weight of about 300 kDa.

Collagen is dissolved in a dilute acid or alkali and may thus be prepared in a liquid phase, and its viscosity increases with an increase in the concentration thereof.

Collagen is suitable for bio-tissue and is a biodegradable material, and is thus diversely used as one of medical materials such as tissue repair agents, skin grafts, bone grafts, and cell cultures.

Meanwhile, collagen extracted from various materials and prepared in a liquid phase is typically filtered in order to serve as a medical material by removing impurities and microorganisms therefrom.

A typical filtration process is performed in a manner in which pressure and fluid flow are formed perpendicular to each other on a filtration membrane, whereby materials larger than the pore size of the filtration membrane are filtered and small materials are passed. During such a filtration process, the filtration target is passed immediately, whereas the material that is not passed may accumulate on the filtration membrane. The filtration efficiency may decrease with an increase in the filtration amount, and the filtration membrane ultimately becomes clogged. The typical filtration process is dependent on the capacity of the filtration target and the area of the membrane, and is limited in that the filtration concentration is low.

Hence, in order to filter a polymeric protein collagen, it has to be prepared in a low-concentration liquid phase. In the case of sterile filtration for removing microorganisms, collagen has to be prepared at a concentration of about 5 mg/mL or less in order to pass through a filtration membrane having a small pore size of 0.22~0.45 µm.

As for methods of highly concentrating the collagen solution prepared at low concentration, a typical evaporate concentration process is problematic because there is concern about thermal degradation of collagen and a long period of time is required to perform the manufacturing process, and also, a concentration process using a volatile solvent is unsuitable for preparing medical materials because the remaining solvent has to be additionally removed.

CITATION LIST (Patent Document 1) Japanese Patent Application Publication No. 2001-200000, which discloses a method of producing marine-derived collagen, wherein the skin tissue of a marine organism is cleaned, collagen is extracted with an organic acid, the resulting solution is passed through a purification membrane to remove impurities, and the solution, extracted using a protease, is subjected to filtration using a purification membrane, a concentration process using a concentration membrane, and a sterile filtration process, thereby yielding concentrated collagen.

(Patent Document 2) Korean Patent Application Publication No. 2014-0091435, which discloses a method of preparing collagen comprising performing a concentration process using a tangential flow filtration device, concentrating the concentrated collagen using a centrifuge, and concentrating the concentrated collagen using a lyophilizer.

(Patent Document 3) U.S. Pat. No. 4,894,441, which discloses a method of preparing collagen comprising extracting biological tissue from the skin of an animal using an organic acid, adding the extracted tissue with sodium chloride to extract collagen, and preparing collagen through tangential filtration.

(Patent Document 4) Japanese Patent Application Publication No. 2011-201837, which discloses a method of preparing a collagen hydrolysate using a porous hollow-fiber membrane having tubular walls formed of a blend of a hydrophobic polymer and a hydrophilic polymer.

(Patent Document 5) (International Patent Document 5) A method of preparing a protein having a triple-helix structure comprising concentrating collagen using a cross-flow filtration process and then purifying the collagen through centrifugation.

DISCLOSURE

Technical Problem

The present invention has been made keeping in mind the problems encountered in the related art, and collagen, which is a protein having low antigenicity and high biodegradability and biocompatibility, is extracted from various animal tissues and may thus be widely utilized not only as a medical material for medical devices and medicines but also as a material for cosmetics or foods.

In order to use collagen as a medical material, the biological safety thereof has to be ensured. When collagen is extracted from the tissue of an animal, an animal-derived virus has to be removed or inactivated to prevent the transfer thereof, and moreover, microorganisms have to be appropriately eliminated.

Typically, a virus is removed by killing it at a high temperature or through filtration using a filter having nanometer-sized pores. However, collagen may be degraded at high temperatures of 37° C. or more and thus the structure of triple-helix strands may unravel into three single strands to thus give gelatin, undesirably losing the fundamental properties of collagen and making it difficult to pass a polymeric protein having a size of 300 nm through a filter for virus removal.

During the extraction of collagen, low-molecular weight materials such as enzymes or sodium chloride have to be removed so as to ensure suitability for medical use.

When collagen is generally used as a liquid dosage form for medical applications, it is required to have a high concentration of 30~60 mg/mL in order to increase the retention time of collagen or to maintain the volume thereof. When collagen is prepared into a solid dosage form through lyophilization, it is required to have a high concentration in order to reduce the capacity of a lyophilizer and the operating time thereof. In order to satisfy the criteria of consumers for a medical material, collagen has to be prepared at a high concentration of 60 mg/mL or more.

Furthermore, with the goal of preparing a medical collagen product in liquid form at high concentration, collagen powder may be used, but sterilization in a powder phase while maintaining the inherent properties and structure of collagen is impossible, and aseptic equipment and a long period of time are required for dissolution in a liquid, sterilization, and concentration.

Technical Solution

The tissue of a mammal is treated with 70% ethyl alcohol for 24 hr and with an acidic solution for 72 hr or more, thereby realizing virus inactivation. Furthermore, microorganisms are removed through filtration using a filter having a pore size of 0.22 μm, thus ensuring safety.

Highly pure collagen is prepared through collagen extraction using pepsin, addition of sodium chloride, filtration, tangential flow filtration, and pH neutralization.

Also, through concentration procedures using tangential flow filtration, pH neutralization, and centrifugation, collagen is highly concentrated to 120 mg/mL, and may be homogenously mixed to thus manufacture various products in liquid, sponge or powder form.

Advantageous Effects

As described hereinbefore, the tissue of a mammal can be produced into aseptic liquid collagen suitable for medical use through virus inactivation, removal of low-molecular-weight materials such as enzymes or sodium chloride using tangential flow filtration, and filtration using a filter having a pore size of 0.22 μm. Furthermore, tangential flow filtration, pH neutralization, and centrifugation are performed, whereby high-concentration liquid collagen of 120 mg/mL can be concentrated and can be used as a material for various medical collagen products while maintaining the liquid phase and aseptic properties thereof.

The preferred embodiments of the present invention for achieving such effects are described in detail below with reference to the accompanying drawings.

DESCRIPTION OF THE REFERENCE NUMERALS IN THE DRAWINGS

Figure 1:
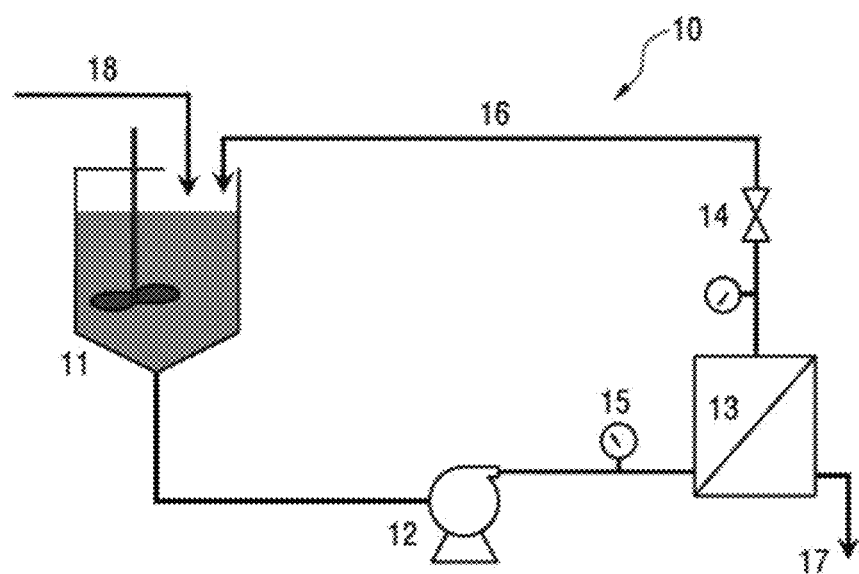
FIG. 1 shows a process of filtering collagen using a tangential flow filtration (TFF) device according to the present invention.

10: tangential flow filtration membrane device 11: storage tank
12: pump 13: tangential flow filtration membrane
14: valve 15: pressure gauge
16: recovery of non-passed material 17: discarding of passed material
18: purified water
21: solution flow direction 22: pressure direction
23: tangential flow filtration membrane 24: non-passed material
25: passed material 31, a: gasket
32, b: fastener 33: pH titration solution inlet
34: pH electrode c: rotary shaft sealing device
d: pH electrode

BEST MODE

The present invention is characterized in that high-concentration liquid collagen, the biological safety of which is ensured and which has high purity, is extracted from the tissue of a mammal so as to be used as a medical material.

Specifically, the tissue of a mammal is washed with clean water and alcohol and then kept frozen. As such, the water is preferably purified water from which microorganisms and ions have been removed, and the alcohol is preferably 70% ethyl alcohol for disinfection.

Before extraction, animal tissue is pretreated in a manner of finely crushing the tissue using a crusher and then immersing the tissue in 70% ethyl alcohol for 24 hr.

The pretreated animal tissue is rinsed with purified water and then extracted.

For primary extraction, enzymatic treatment is performed by placing the tissue and a protease in purified water at a pH of 1.5 to 2.5 and then performing stirring for 72 hr or more.

Here, pH titration may be carried out using any acidic solution such as phosphoric acid or hydrochloric acid, and the protease is preferably pepsin, which is able to remove the terminus of collagen for causing an immune response in the human body without damaging the triple-helix structure of collagen.

If the pH for enzymatic treatment is less than 1.5, it is unsuitable for chemical resistance of a filter for use in the subsequent filtration process. On the other hand, if the pH exceeds 2.5 or the reaction time is less than 72 hr, the virus inactivation effect may decrease.

The pretreatment process including immersion in ethyl alcohol for 72 hr or more and the enzymatic treatment process at a pH of 2.5 or less for 72 hr or more enable the inactivation of viruses that may be present in the animal tissue, thus ensuring biological safety.

For secondary extraction and purification, the solution subjected to enzymatic treatment undergoes a salt treatment process in a manner such that it is reacted with sodium chloride at a concentration of 0.5~0.9 M. This is because each protein is able to aggregate at a specific salt concentration and also because collagen may aggregate and float at the above salt concentration, whereby the other non-aggregated impurities are discarded to thus increase the purity of collagen.

The aggregated collagen is dissolved again in purified water so as to perform a filtration process.

For tertiary purification, the solution is first filtered using a filter having a pore size of 2.0~0.5 μm, and is then treated using a TFF device so that low-molecular-weight materials such as pepsin, sodium chloride, etc. may be removed from the solution.

The TFF device preferably includes a 50~150 kDa molecular-weight-cutoff (MWCO) filtration membrane. The 150 kDa or less MWCO filtration membrane functions to prevent the loss of collagen of about 300 kDa, and the 50 kDa or more MWCO filtration membrane functions to remove pepsin of about 35 kDa.

Figure 2:
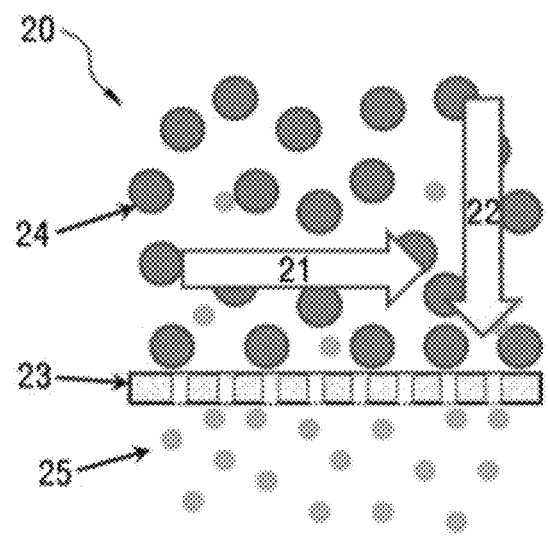
FIG. 2 shows a tangential flow filtration membrane according to the present invention.

The filtration process using the TFF device is performed using a storage tank 11, a pump 12, a filtration membrane 13, a pressure gauge 15 and a valve 14. The solution in the storage tank is transferred to the filtration membrane via the pump so that collagen larger than the pore size of the filtration membrane is not passed but is recovered into the storage tank and also so that impurities smaller than the pore size are passed through the pores and thus removed. The purified water is added in an amount corresponding to the amount of the impurities removed through the pores in the filtration membrane. This procedure is repeated, whereby the purity of collagen may be increased while maintaining the flowability of the collagen solution in the storage tank (FIGS. 1 and 2). The results of purification using the TFF device may be confirmed through various methods, among which the removal of sodium chloride can be found through osmotic measurement (Example 3).

The TFF device is used for a concentration process, in addition to the purification process. When the filtration is repeated without the addition of purified water at a time point at which the removal of impurities is completed, water is removed via the pores, and thus the amount of collagen in the storage tank is increased. Accordingly, the amount of collagen may be concentrated to 10 mg/mL, and collagen thus obtained may be utilized in fields that do not require high concentration, such as those of cosmetic materials.

However, since the viscosity of collagen is increased with an increase in the concentration thereof, when concentration process to 10 mg/mL or more is carried out, collagen may accumulate on the filtration membrane, and the flowability of the collagen solution may significantly decrease, thus lowering the yield and requiring a long processing time. In order to produce collagen for medical use, it is concentrated to 5 mg/mL or less, thereby ensuring flowability and viscosity suitable for sterile filtration.

Figure 3:
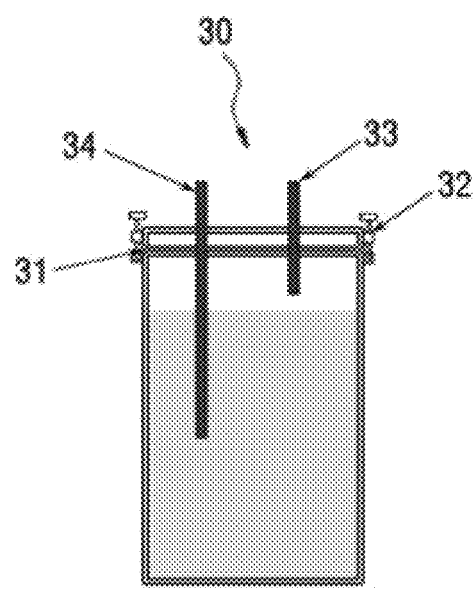
FIG. 3 shows the structure of a neutralization tank according to the present invention.

After the completion of purification and concentration using the TFF device, the resulting solution is filtered through a filter having a pore size of 0.22 μm and then transferred to a neutralization tank. Here, the sterile filter and the neutralization tank should be in a sterile state. In particular, the neutralization tank should be able to be sealed using a gasket 31 and a fastener 32 and should include a pH titration solution inlet, a pH measurement electrode, and a jacket for adjusting the temperature of the solution (FIG. 3).

The collagen solution from which microorganisms have been removed through sterile filtration is purified and concentrated once more using a neutralization process. The neutralization process is performed in a manner in which the pH of the collagen solution is adjusted to 6.0~8.0 using a pH titration solution such as sodium hydroxide or hydrochloric acid and the temperature of the solution is adjusted to 25~35° C. to thereby aggregate collagen.

During the neutralization process, if the pH of the solution falls out of the above range or the temperature of the solution is low, collagen may not sufficiently aggregate. On the other hand, if the temperature of the solution is high, the triple-helix structure may unravel due to thermal degradation.

Collagen is aggregated through the neutralization process, and the solution, which is not aggregated, is removed, whereby the amount of a concentrating target may be decreased before a concentration process using centrifugation, making it easy to separate water and collagen from each other, and the concentration process may be performed within a short time using a low centrifugal force, ultimately constructing an apparatus that enables mass production at relatively low cost.

The collagen, which is aggregated through neutralization, is placed in a sterilized centrifugation vessel, and is then concentrated for 5 min at a gravitational acceleration of 4,000~6,000 g using a centrifuge.

If the above process is conducted using a lower centrifugal force or for a shorter time, the yield of collagen may decrease or the final concentration value may decrease. On the other hand, if higher gravitational acceleration is applied for a long time, a high-performance expensive centrifuge suitable therefor is required, and the production time may increase.

Figure 4:
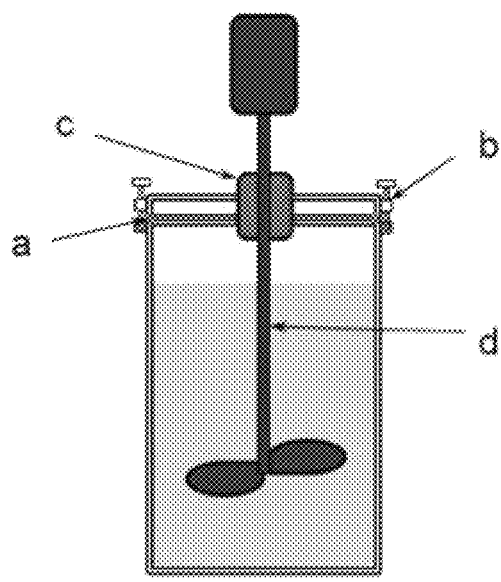
FIG. 4 shows a mixer.

The collagen thus concentrated is placed in a mixer (FIG. 4) having a closed structure and is then homogeneously mixed, thus obtaining high-concentration collagen for use in a medical material. Here, the concentration of collagen may be adjusted by adding water from which microorganisms and exothermic materials have been removed, depending on the desired purposes, and collagen having a high concentration of 120 mg/mL may be obtained under the above conditions.

During the above mixing process, an acidic solution such as hydrochloric acid is added as the pH titration solution so that the pH of the solution is adjusted to 1.5~5.5. The solution having an adjusted pH may be stored stably in a homogenous state for a long period of time. If the pH thereof is too low, it is difficult to titrate the pH to a neutral value in order to prepare a medical product. On the other hand, if the pH thereof is higher than 5.5, collagen may aggregate again, making it difficult to maintain a uniform concentration.

Depending on the needs, the collagen, obtained through extraction, purification, concentration and mixing processes, may be mixed and diluted with a mixing solvent such as water, an isotonic solution, platelet-rich plasma (PRP), or hyaluronic acid to thus give a liquid product, and the concentrated collagen may be provided in the form of a solid product through lyophilization.

In particular, a liquid product may be provided in a state in which biological safety is ensured in the absence of viruses and microorganisms within a minimal clean-room facility that enables mixing, filling, and packing.

[Example 1]
Preparation and Use of Medical Collagen Using Pig Skin Tissue

1) Pig skin tissue is washed with purified water and alcohol and then kept frozen at −20° C. or lower.

2) The pig skin tissue is finely crushed.

3) The crushed skin tissue is immersed in 70% ethyl alcohol for 24 hr. (Primary Virus Inactivation)

4) The tissue is rinsed by being placed in purified water, titrated to an acidic pH (pH 1.5~2.5) using phosphoric acid, and is then reacted with stirring for 72 hr or more by the addition of pepsin. (Secondary virus inactivation)

Here, the amount of pepsin is ¼~1/10 of the weight of the skin tissue.

5) The collagen is added with sodium chloride at a concentration of 0.5~0.9 M, stirred and aggregated, after which the non-aggregated solution is removed.

6) The aggregated collagen is dissolved in water titrated at a pH of 1.5~4.0 and then filtered using a filter having a pore size of 2.0~0.5 μm.

7) In order to obtain collagen suitable for medical use, low-molecular-weight materials such as pepsin and sodium chloride are removed from the solution using a TFF device.

The TFF device preferably includes a 50~150 kDa MWCO filtration membrane, and purified water is added in an amount corresponding to the amount removed through the pores of the filtration membrane so that the amount of the collagen solution in the storage tank is maintained to thus ensure flowability.

8) After the completion of removal of low-molecular-weight materials such as pepsin and sodium chloride, the supply of purified water is stopped and TFF is maintained, and thus a concentration process is carried out. As such, the concentration of collagen is adjusted to 5 mg/mL or less so as to pass through a filter having a pore size of 0.22 μm.

9) To remove microorganisms, filtration is performed using a filter having a pore size of 0.22 μm.

10) The solution from which microorganisms have been removed is transferred to a sterilized neutralization tank. The neutralization tank has to be sterilized and has to have a sealed structure able to maintain a sterile state, and includes a pH titration solution inlet and a pH measurement electrode.

11) To aggregate collagen, the collagen solution is allowed to stand for a time period ranging from 4 hr to one day under the condition that it is titrated to an approximately neutral pH (pH 6.0~8.0) using hydrochloric acid (HCl) and a sodium hydroxide solution (NaOH) and the temperature thereof is adjusted to 25~35° C.

12) The non-aggregated solution is discarded and the aggregated collagen is placed in a centrifugation vessel and then in a centrifuge, and is centrifuged at a gravitational acceleration of 4,000~6,000 g, thereby concentrating collagen.

13) Water is decanted from the centrifugation vessel and the concentrated collagen, having been separated from the water, is placed in a mixer and then stirred, thus obtaining collagen having a concentration of about 120 mg/mL.

As such, the collagen thus obtained is mixed with an acidic solution such as hydrochloric acid to adjust the pH thereof to 1.5~5.5, whereby the collagen may be stored at a homogeneous concentration.

14) The collagen, from which microorganisms have been removed and which has high purity, is prepared in a state in which the properties of collagen are maintained, using the above method, and is thus suitable for medical use, and may have a high concentration of 120 mg/mL and may thus be applied to various products.

For example, collagen may be provided in the form of a product that may be injected into the body in a manner in which the collagen is mixed with an additive so as to possess the same composition as the saline in the human body while maintaining a liquid phase and is then charged in a pre-filled syringe.

[Example 2]
Verification of Virus Inactivation

The virus inactivation process during the production process of Example 1 was performed through three simulations to thus verify the virus inactivation.

Adopted as indicator viruses were PEDV (Porcine epidemic diarrhea virus), PRV (Porcine rotavirus), PPV (Porcine parvovirus), and Pseudorabies virus, depending on the genotypes, presence or absence of enveloped lipids, and resistivity.

The adopted four kinds of viruses are inoculated into the crushed pig tissue and then incubated in 70% ethyl alcohol for 24 hr and in an acidic solution having a pH of 2.5, adjusted by the use of phosphoric acid, for 72 hr in order to reproduce the pretreatment and enzymatic treatment procedures of the actual preparation method.

The samples in which the virus inactivation process was reproduced are compared before and after treatment through quantitative viral analysis.

The results of three simulations under the same conditions were the same. All viruses were detected to a detection threshold or less, and the log reduction factor for each virus inactivation process was measured to be a 2-log reduction factor or more corresponding to a typical standard that is regarded as effective for virus inactivation. The maximum cumulative log reduction factors of PEDV, PRV, PPV, and Pseudorabies virus per process were 6.75, 9.75, 8.75, and 8.75, respectively, from which strong virus inactivation effects can be concluded to have been exhibited.

TABLE 1

| Preparation process | Reduction factor ($Log_{10}TCID_{50}$) | | | |
| --- | --- | --- | --- | --- |
| | PEDV | PRV | PPV | Pseudorabies virus |
| Pretreatment (70% ethyl alcohol, 24 hr) | ≥4.05 | ≥5.55 | ≥5.05 | ≥5.05 |
| Enzymatic treatment (pH 2.5, 72 hr) | ≥2.70 | ≥4.20 | ≥3.70 | ≥3.70 |
| Maximum cumulative log reduction factor | ≥6.75 | ≥9.75 | ≥8.75 | ≥8.75 |

[Example 3]
Removal of Sodium Chloride Using TFF

After the enzymatic treatment, treatment with sodium chloride, and filtration using a filter having a pore size of 2.0~0.5 μm of Example 1, TFF was conducted using a 100 kDa MWCO filtration membrane.

Here, purified water was added in an amount corresponding to the amount removed through the pores in the filtration membrane, and this procedure was repeated, whereby the flowability of the collagen solution in the storage tank was ensured and low-molecular-weight materials such as pepsin and sodium chloride were removed, and the total amount of purified water that was added was five times the initial amount of the collagen solution.

The above TFF process was repeated three times and the results of removal of low-molecular-weight materials were verified by measuring osmotic pressure using sodium chloride, chosen because it is a typical material.

Consequently, individual removal rates were 96.2%, 96.1%, and 96.4%, and the average removal rate was determined to be 96.2%. Thereby, the removal of low-molecular-weight materials via TFF is effective, and sodium chloride shows an osmotic pressure of 31~33 mOsm, which is lower than 285 mOsm, which is the plasma osmotic pressure, and may be used as a medical material in a mixture with an isotonic solution, as necessary.

TABLE 2

| Case | Osmotic pressure (mOsm) | | Removal rate |
|---|---|---|---|
| | Before TFF | After TFF | |
| 1 | 840 | 32 | 96.2% |
| 2 | 846 | 33 | 96.1% |
| 3 | 861 | 31 | 96.4% |
| | Average | | 96.2% |

[Example 4]
Collagen concentration by stepwise concentration process

According to the preparation method of Example 1, 5 kg of pig skin and 1 kg of pepsin were used, and the concentration of collagen for each step was measured when a concentration process was performed to ½ of the initial amount upon TFF.

The concentration from the enzymatic treatment process to the filtration process using a filter having a pore size of 2.0~0.5 µm fell in the range of 1.6~2.4 mg/mL for each case, and the concentration was 3.2~4.8 mg/mL after the removal of low-molecular-weight materials during TFF.

This is performed to realize passage through a sterile filtration filter having a pore size of 0.22 µm after TFF. When the concentration is adjusted to 2 mg/mL or less, the amount of the collagen solution is increased and thus the volume of the neutralization tank is enlarged. After the neutralization process, a long period of time is required to perform a concentration process using centrifugation, ultimately increasing production costs. On the other hand, when the concentration of the collagen solution was adjusted to 5 mg/mL or more, viscosity is increased, making it difficult to pass through the sterile filter having a pore size of 0.22 µm, whereby the sterile filter may be clogged early, undesirably causing the loss of collagen and using a large filter. For this reason, the concentration value before a sterile filtration process is preferably set to the range of 2~5 mg/mL.

The water, which was not aggregated during the neutralization process, was primarily removed, whereby collagen could be concentrated to 5.6~6.7 mg/mL from 3.2~4.8 mg/mL. Accordingly, collagen is concentrated about 1.4- to 1.8-fold compared to the concentration value before the neutralization process. Thus, during the concentration process using centrifugation, initial capacity may be reduced, advantageously resulting in industrial applicability in which the centrifuge capacity and the processing time may be reduced.

Finally, the collagen solution aggregated after the neutralization process is concentrated using centrifugation, whereby high-concentration collagen may be obtained in the concentration range of 114.6~122.3 mg/mL for each case, which is suitable for use as a material for a medical liquid collagen product having a concentration of 30~60 mg/mL and which is also able to reduce the capacity of a lyophilizer and the operating time thereof when a solid formulation is produced using lyophilization.

TABLE 3

| Production process | Collagen concentration per production process (mg/mL) | | | |
|---|---|---|---|---|
| | A | B | C | D |
| Case 1 | 1.6 | 3.2 | 5.6 | 114.6 |
| Case 2 | 2.4 | 4.8 | 6.7 | 122.3 |
| Case 3 | 2.1 | 4.1 | 5.9 | 121.1 |

* Note)
A: enzymatic treatment~filtration (with a pore size of 2.0~0.5 µm)
B: tangential flow filtration (concentration process after removal of low-molecular-weight material)
C: neutralization (after removal of non-aggregated solution)
D: concentration process using centrifugation Although the specific embodiments of the present invention have been disclosed for illustrative purposes, those skilled in the art will appreciate that various modifications, equivalents and substitutions are possible, without departing from the scope and spirit of the invention as disclosed in the accompanying claims.

The invention claimed is:

1. A method of producing high-concentration collagen for use as a medical material, the method comprising the sequential steps of:
   (a) washing tissue of a mammal;
   (b) crushing the washed tissue, immersing the crushed tissue in 70% ethyl alcohol for 24 hours, placing the tissue to enzymatic treatment with stirring in purified water titrated to a pH of 1.5-2.5 using phosphoric acid, and allowing the tissue to react with an amount of pepsin having ¼-1/10 of a weight of the tissue by stirring for at least 72 hours, thereby inactivating viruses and extracting collagen;
   (c) adding sodium chloride to the extracted collagen at a concentration of 0.5-0.9 M, performing stirring, aggregating collagen, and removing a non-aggregated solution;
   (d) dissolving the aggregated collagen in purified water to give a collagen solution, filtering using a filtration membrane having a pore size of 0.5-2.0 µm and concentrated by removing low-molecular-weight materials having a smaller size than pores of the filtration membrane, including pepsin and the sodium chloride, from the collagen solution using a tangential flow filtration device;
   (e) subjecting the collagen concentrated using the tangential flow filtration device to sterile filtration, aggregating the collagen by adjusting pH to 6.0-8.0 in a neutralization tank, and concentrating the collagen by removing a non-aggregated solution; and
   (f) further concentrating the concentrated collagen using a centrifuge, and then stirring the concentrated collagen using a mixer,
   wherein the collagen concentrated through neutralization is centrifuged at a gravitational acceleration 4,000-6,000 g producing the concentrated collagen, and is stirred using a mixer, thus obtaining high-concentration collagen of at least 120 mg/mL.

2. The method of claim 1, wherein the tangential flow filtration device comprises a 50-150 kDa molecular-weight-cutoff filtration membrane, purified water is added in an amount corresponding to an amount of the solution that is removed so as to maintain flowability, the low-molecular-weight materials smaller than a pore size of the filtration membrane are removed, and collagen is concentrated to 5 mg/mL or less so as to allow the low-molecular-weight materials to pass through a filter having a pore size of 0.22 µm.

3. The method of claim 1, wherein the concentrated collagen produced using the tangential flow filtration device is allowed to stand for 4-24 hours under a condition that the collagen is adjusted to a neutral pH (6.0-8.0) and is maintained at a temperature of 25-35° C., whereby the aggregated collagen is recovered and centrifuged using a centrifuge, thereby being concentrated.

* * * * *